Figure 1:
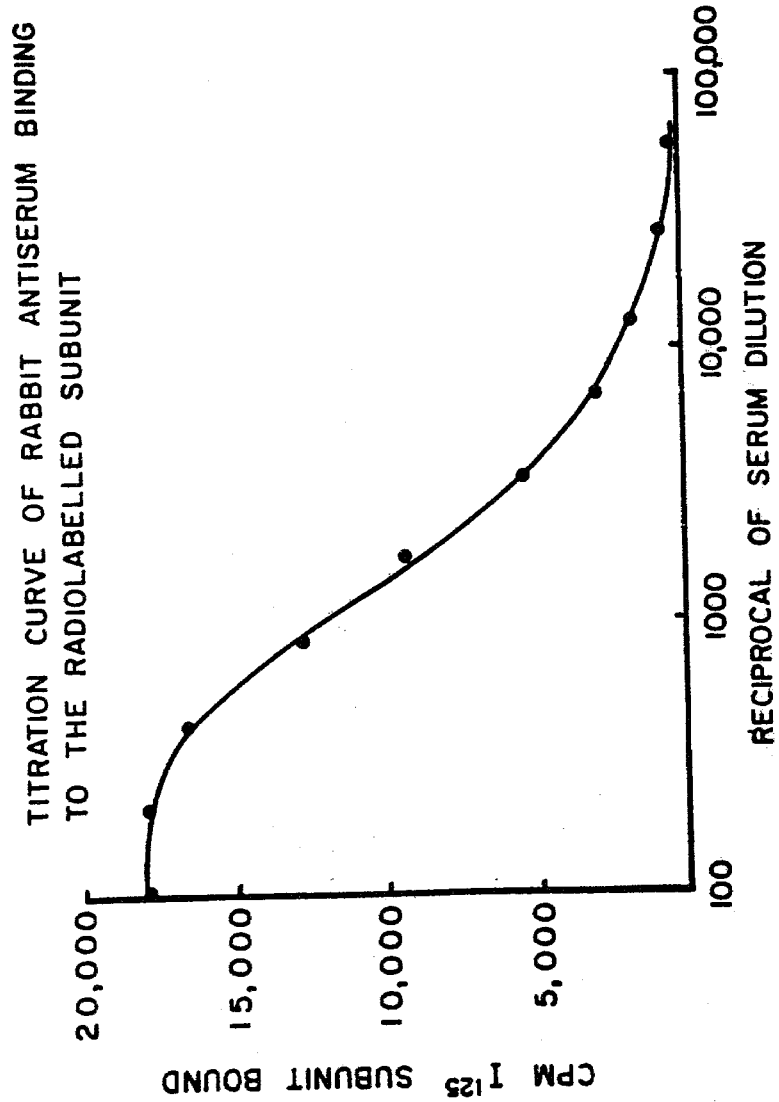

United States Patent [19]

McDonald

[11] 4,248,964

[45] Feb. 3, 1981

[54] DETECTION AND QUANTITATION OF NEISSERIA VIA RADIOIMMUNOASSAY OF AN ENZYME PRESENT IN NEISSERIA BACTERIA

[75] Inventor: Hugh C. McDonald, Horseheads, N.Y.

[73] Assignee: Corning Glass Works, Corning, N.Y.

[21] Appl. No.: 837,360

[22] Filed: Sep. 28, 1977

[51] Int. Cl.$^3$ .............................................. C12Q 1/66
[52] U.S. Cl. ........................................ 435/7; 424/12; 23/230 B
[58] Field of Search ............................ 435/7; 424/12; 23/230 B

[56] References Cited

U.S. PATENT DOCUMENTS

| | | | |
|---|---|---|---|
| 3,875,011 | 4/1975 | Rubenstein et al. | 435/7 |
| 3,974,269 | 8/1976 | Maley | 435/7 |
| 4,029,756 | 6/1977 | Gaafar | 435/7 |
| 4,066,744 | 1/1978 | Price et al. | 23/230 B |

*Primary Examiner*—Alvin E. Tanenholtz
*Attorney, Agent, or Firm*—William E. Maycock; Clinton S. Janes, Jr.

[57] ABSTRACT

This invention relates to a method for detecting Neisseria bacteria by means of a radioimmunoassay for a bacterial protein. More specifically, this invention employs the method of radioimmunoassay in which a purified enzyme or enzyme related protein from Neisseria cells is labelled and is mixed with the unknown sample which represents a bacterial lysate. A known amount of antibody specific for the enzyme is added to the mixture and forms complexes with the labelled and unlabelled enzyme present. After a suitable reaction period, the labelled enzyme-antibody complex is separated from the mixture, and its radioactivity is determined. The presence and amount of enzyme in the unknown sample is calculated by relating the radioactivity count to a standard curve prepared with known quantities of unlabelled enzyme.

14 Claims, 2 Drawing Figures

4,248,964

DETECTION AND QUANTITATION OF NEISSERIA VIA RADIOIMMUNOASSAY OF AN ENZYME PRESENT IN NEISSERIA BACTERIA

RELATED APPLICATIONS

U.S. patent application Ser. No. 837,366, filed of even date by H. H. Weetall entitled "Detecting Neisseria Bacteria", now U.S. Pat. No. 4,166,765, patent application Ser. No. 837,365, filed of even date by H. H. Weetall entitled "Comparative Test for Neisseria," now U.S. Pat. No. 4,111,752, patent application Ser. No. 837,364, filed of even date by H. H. Weetall entitled "Detection of Neisseria Bacteria by Immunoassay," U.S. patent application Ser. No. 837,363, filed of even date by H. H. Weetall entitled "Immunoassay of Neisseria Bacteria Via $(NH_4)_2SO_4$ Precipitation", now U.S. Pat. No. 4,140,581, U.S. patent application Ser. No. 837,362, filed of even date by H. H. Weetall entitled "Immunological Detection of Neisseria Bacteria Via Labelled Antibodies," now U.S. Pat. No. 4,188,371, and U.S. patent application Ser. No. 837,361, filed of even date by M. M. Takeguchi and H. H. Weetall entitled "Transport System for Clinical Specimens," now U.S. Pat. No. 4,150,950, each of said applications being assigned to the assignee of the instant application.

BACKGROUND OF THE INVENTION

The importance of being able to quickly and accurately determine the presence of Neisseria bacteria, particularly *Neisseria gonorrhoeae*, is well-appreciated. Conventional tests for detecting the presence of organisms such as *N. gonorrhoeae* require the preparation of bacteria cultures or the use of serological methods. Such tests, however, have well-recognized limitations. See, for example, the publication "International Symposium on Gonorrhea," B. B. Diena, Ed., a collection of papers presented at the October, 1973 International Symposium on Gonorrhea sponsored by the Health Protection Branch, Health and Welfare Canada, Ottawa, especially at page 34 et seq.

A relatively simple and quick enzymatic test for the presence of Neisseria bacteria is disclosed in the related patent application cited above entitled "Detecting Neisseria Bacteria". That test is based upon an enzyme assay for the enzyme, 1,2-propanediol dehydrogenase, which enzyme is specific to Neisseria bacteria. Thus, an enzyme was found in Neisseria which oxidizes 1,2-propanediol and reduces nicotinamide-ademine-dinucleotide (NAD) to NADH. The composition and structure of that enzyme are not fully understood nor has any identification therefor been found in the literature. Accordingly, its capability for oxidizing 1,2-propanediol and reducing NAD led to the adoption of the term 1,2-propanediol dehydrogenase therefor. That designation will be used throughout this specification.

In another related application cited above entitled "Detection of Neisseria Bacteria by Immunoassay" is disclosed the use of antibodies to inhibit the activity of the enzyme 1,2-propanediol dehydrogenase. And in yet another application cited above entitled "Immunoassay of Neisseria Bacteria Via $(NH_4)_2SO_4$ *Precipitation*" is disclosed a modification of that method wherein $(NH_4)_2SO_4$ precipitation of the antigen-antibody complex acts to concentrate the enzyme, remove interfering materials, and thereby improve the speed and precision of the assay.

In another related application cited above entitled "Immunological Detection of Neisseria Bacteria Via Labelled Antibodies," is disclosed a method for detecting N. gonorrhoeae cells that uses a radiolabelled antibody specific to the enzyme in two particular embodiments of radioimmunoassay techniques.

The instant disclosure is concerned generally with a process for detecting the presence of Neisseria bacteria by means of a radioimmunoassay (RIA) technique. It is particularly useful in detecting *N. gonorrhoeae*.

The reaction between an antibody and its homologous antigen is recognized as a specific biochemical reaction. In many instances, this reaction occurs even when the antigen is modified by the addition of a radioactive tracer. The antibody-antigen complexes then formed are radioactive and by various known means can be separated from uncomplexed reactants. As the measurement of radioactivity is a known and sensitive procedure, a quantitative assay for any protein to which a specific antibody is available is possible. In general such an assay requires antibody, purified antigen, and radiolabelled antigen. A known amount of antibody is mixed with a known amount of radiolabelled antigen and, after a suitable reaction time, the radioactive antibody-antigen complexes are separated from the uncomplexed radiolabelled antigen. This separation often occurs via a precipitation reaction that results when an antiglobulin antiserum is added which is specific for the gamma globulin in which the first antibody was prepared. The precipitate is collected by centrifugation and its radioactivity or the radioactivity in the supernatant solution is determined. Using the above procedure, the concentration of antigen can be determined by use of a standard reference curve. The curve is generated by mixing known amounts of antibody and labelled antigen with varying amounts of unlabeled antigen. In the reaction that occurs between the antibody and the two forms of antigen, the amount of radioactivity in the antibody-antigen complex is directly related to the concentration of unlabelled antigen in the reaction mixture. This occurs because the two forms of antigen are competing for the same, limiting amount of antibody. The amount of antigen in an unknown is determined by mixing a sample of the unknown with known amounts of antibody and labelled antigen. The radioactivity in the antibody-antigen complex is then related to the standard curve prepared with known amounts of unlabelled antigens.

In summary, a competition reaction between labelled antigen and unlabelled antigen for a limiting amount of antibody is established and the amount of radioactivity in the resulting antibody-antigen complexes is directly related to the concentration of unlabelled antigen in the starting reaction mixture.

DRAWINGS

FIG. 1 represents a titration curve of antiserum binding to radiolabelled enzyme or enzyme related protein.

Figure 2:
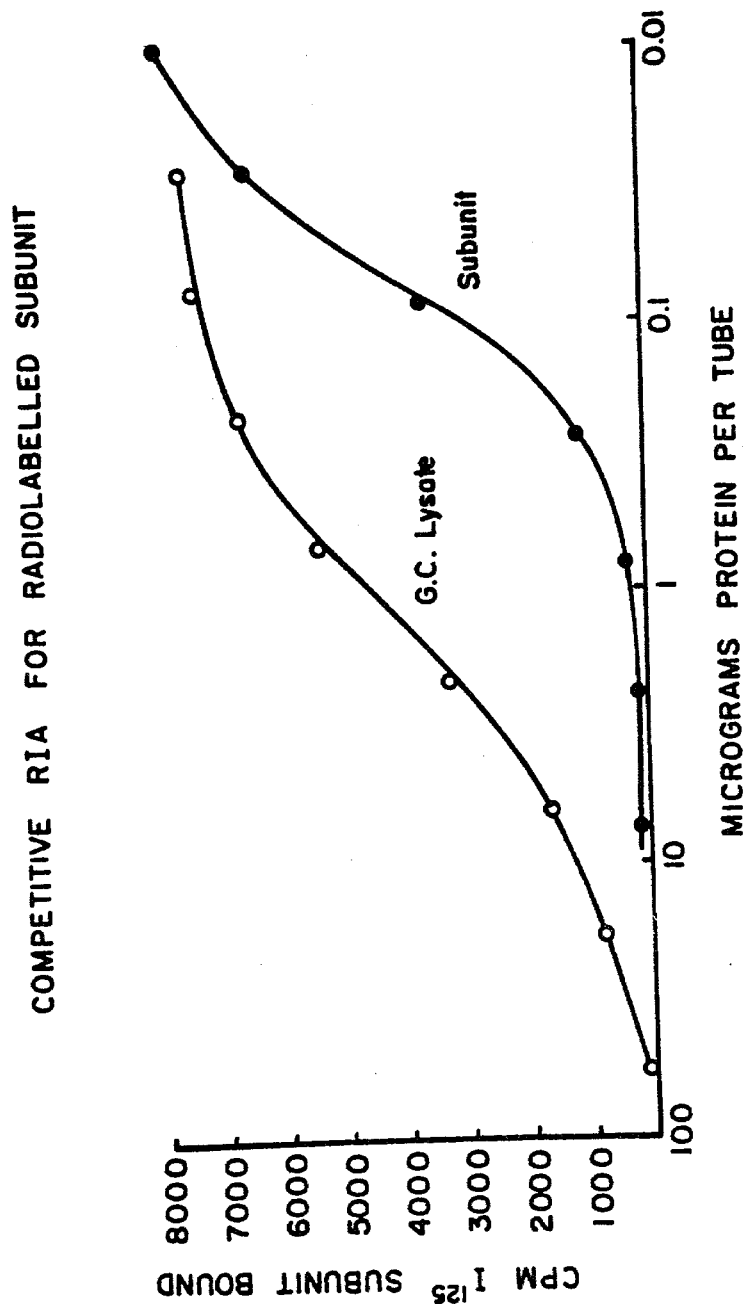

FIG. 2 sets out curves illustrating the competitive RIA for radiolabelled enzyme or enzyme related protein.

SUMMARY OF THE INVENTION

Defined in its broadest terms, the method of the instant invention contemplates the following four general steps:

(1) bringing radiolabelled 1,2-propanediol dehydrogenase or enzyme related protein or fragment released from Neisseria bacteria during lysis thereof into contact with a lysate of the sample to be tested;

(2) admixing an antiserum specific to 1,2-propanediol dehydrogenase therewith and incubating said mixture;

(3) separating the radiolabelled enzyme-antibody complex from the uncomplexed reactants in said mixture; and then (4) monitoring either or both portions of the mixture for the presence of radiolabelled enzyme or radiolabelled enzyme related protein or fragment.

The exemplary embodiments of the invention reported infra, representing preferred practices thereof, utilize the following schedule of steps:

(1) preparing an antiserum specific to 1,2-propanediol dehydrogenase;

(2) purifying 1,2-propanediol dehydrogenase, or a protein related to 1,2-propanediol dehydrogenase;

(3) preparing radiolabelled 1,2-propanediol dehydrogenase or radiolabelled enzyme related protein or fragment;

(4) preparing lysates of bacteria to be tested;

(5) mixing and incubating lysates with antibody and radiolabelled enzyme or radiolabelled enzyme related protein;

(6) separating the antibody-antigen complexes by the addition of an antiglobulin reagent which effects a precipitation, (7) monitoring the precipitate or the supernatant solution for the presence of radiolabelled enzyme or radiolabeled enzyme related protein.

In the preferred embodiment, a protein or fragment related to 1,2-propanediol dehydrogenase will be radiolabelled. However, the basic inventive technique is also operable with the purified, intact enzyme.

SPECIFIC EMBODIMENTS

A method for preparing an operable lysate is disclosed in the above-cited related application entitled "Detecting Neisseria Bacteria" and that method can also be employed here. The objective of the lysing practice is to release intracellular content, including enzymes, from a sample, e.g., human body fluid or exudate. The lysing procedure need only be conducted in such a manner and under such conditions that denaturing of the enzyme of interest is avoided.

*N. gonorrhoeae* cells were cultivated in suspension culture by known means. For lysate preparations, a suspension of *N. gonorrhoeae* bacteria was prepared in 0.03 M TRIS buffer, pH 9.0. The suspension was compounded in a manner to contain about $10^5$ bacteria, as determined via an absorbency of 0.1 on a Spec 20 spectrophotometer. To 50 ml of the suspension at 0° C. were added 5 ml of a 0.1% solution of egg-white lysozyme (Biozyme Laboratories) prepared in 0.03 M TRIS buffer, pH 9.0. This bacteria-buffer-lysozyme mixture was mixed together and allowed to stand briefly. Then 5 ml of a 0.1% solution of EDTA (ethylene diamine tetraacetic acid) in 0.03 M TRIS buffer, pH 9.0, were added and the resulting mixture agitated in a shaker bath for 10 minutes at 12 reciprocating cycles/five seconds. The EDTA acts as a chelating agent to bond with any divalent metal ions present which might interfere with the activity of the enzyme. Other chelating agents may be used so long as the bacteria-buffer-lysozyme reaction is not deleteriously affected. Thus, the inclusion of EDTA is not mandatory but comprises a useful precaution. Lysis was permitted to continue for one hour at 0° C. Thereafter, the mixture was centrifuged for 10 minutes at 5000 rpm and the supernatant decanted off, this supernatant constituting the lysate. Lysates of other bacteria were prepared similarly.

The 1,2-propanediol dehydrogenase enzyme contained within the supernatant was purified utilizing an affinity column as described, e.g., by Lee, Chi-Yu, D. A. Loppi, B. Wermuth, J. Everse, and N. O. Kaplan, Arch. Biochem. Biophys. 163, 561–569, 1974. Thus, to a column containing approximately 60 ml agarose-AMP (adenosine monophosphate) are added 30 ml of the supernatant diluted in half with 0.02 M $KH_2PO_4$, pH 6.0. The supernatant is washed through and followed with more buffer until the optical density at 280 nm is near zero when viewed with a Perkin-Elmer double beam spectrometer. The enzyme is eluted with 0.5 mM NADH (40 mg/100 ml) in 0.02 M $KH_2PO_4$, pH 6.0. The active fractions are combined and lyophilized either before or after dialysis.

The enzyme related protein was isolated by elution from polyacrylamide gels following electrophoresis of purified 1,2-propanediol dehydrogenase according to the procedure of Maizel described in "Methods in Virology," 5, 179–246, Academic Press, Inc., New York, 1971. In the following exemplary embodiment, to 0.1 ml of purified enzyme in 0.01 M sodium phosphate buffer, pH 7.0, containing 0.1 mg protein were added 0.01 ml of a 10% solution of sodium dodecyl sulfate, and 0.001 ml of 2-mercaptoethanol. The sample was heated at 100° C. for 1 minute and then applied to a 9 cm long gel having an acrylamide monomer concentration of 7.5%. The sample was electrophoresed at a constant 8 ma current using commercially available electrophoretic apparatus and power supply. After electrophoresis, the gel was removed from the apparatus and placed in an ice bath at 4° C. The location of the major protein band was visualized in the gel as a hazy white band and that area was excised following the procedure described by Wallace et al. in Analytical Biochemistry, 61, 86–92, 1974. The cut out gel section was placed in 0.5 ml sodium phosphate buffer, pH 7.5, and the entrapped protein was eluted into the buffer during a 24 hour room temperature incubation. The protein recovered in the eluting buffer was considered the enzyme related protein and probably represents the subunit component of 1,2-propanediol dehydrogenase. Thus, the term subunit, as used in this disclosure, refers to the 1,2-propanediol dehydrogenase related protein isolated by gel elution as described above.

The subunit can be labelled with an isotope of iodine, e.g., $I^{125}$, following the general chloramine T procedure described by Greenwood, F. C., Hunter, W. M., and Glover, J. S., in "The Preparation of I-131 Labeled Human Growth Hormone of High Specific Radioactivity," Biochem. 89, 114–123, 1963. For use in the succeeding exemplary embodiments, the following procedure was employed.

To a small glass reaction vessel held at room temperature were added 0.02 mg subunit in 0.05 ml 0.5 M sodium phosphate buffer, pH 7.5, 1.0 millicuries of I-125, and 0.01 ml of chloramine T solution (1.25 mg/ml in 0.5 M sodium phosphate buffer, pH 7.5). The solution was agitated 15 seconds and then quenched via the addition of 0.02 ml of sodium metabisulfite solution (1.25 mg/ml in 0.5 M sodium phosphate buffer, pH 7.5).

Thereafter, a column was prepared employing a 10 ml glass pipette packed with Sephadex G-25, a gel filtration medium marketed by Pharmacia Fine Chemicals, Inc., Piscataway, N.J. The column was washed with 0.05 M phosphate-buffered saline, pH 7.3, a 1 ml solution of 5% bovine serum albumin, and then equilibrated with 5 column volumes of phosphate-buffered saline. The iodination reaction mixture was then allowed to flow into the column and 1.0 ml fractions were collected. Elutrification was performed with phosphate buffered saline and labeled protein was removed from the column at fractions 4–5 as monitored by a portable ratometer (small Gieger Counter). Bovine serum albumin was added to the pooled fractions containing radiolabelled protein to a final concentration of 0.5%.

An antiserum is prepared against 1,2-propanediol dehydrogenase in a known manner via the immunization of rabbits. The globulin fraction of such antiserum can also be used. A goat anti rabbit globulin antiserum was used as the precipitating agent of the antibody-antigen complexes and was prepared by known methods.

EXAMPLE 1

Titration Curve of Rabbit Antiserum Bonding To The Labeled Enzyme Related Protein Serial twofold dilutions of rabbit antiserum were prepared in a 0.05 M phosphate buffer, pH 7.5, which contained 0.01% Triton-X-100 (a detergent marketed by Rohm and Haas, Philadelphia, Pa.), 0.03% ethylene diamine tetraacetic acid, and 1% normal rabbit serum. All assays used this buffer. The reactants in the radioimmunoprecipitation test are: 0.350 ml of buffer, 0.1 ml each serial dilution of antisera, and 0.1 ml of labelled subunit diluted to contain about 25,000 counts per minute. After an overnight incubation step at 4° C., bound label was separated from free by the antiglobulin precipitation reaction occurring after the addition of goat anti rabbit globulin reagent. After a suitable reaction time for the precipitate to form, all reaction tubes were centrifuged, and the precipitates counted in a Gamma Scintillation Counter. FIG. 1 shows that the labelled protein is 75% precipitable with a 1:100 dilution of antiserum. The percent of label precipitable decreases as the serum dilution increases and a typical titration curve is generated. The 50% bonding point is effected by a 1:1000 serum dilution.

EXAMPLE 2

Displacement of Radiolabelled Enzyme Related Protein From Rabbit Antiserum

The radioimmunoassay for the iodinated subunit uses the following reagents: 0.300 ml buffer, 0.05 ml test sample, 0.1 ml rabbit antiserum diluted 1:1000, and 0.1 ml of label containing about 15,000 counts per min. All other steps are as described in Example 1. The results are calculated as the percent displacement the unknown sample effects from a base level of bound label resulting when no unlabelled enzyme is added.

FIG. 2 shows displacement curves for the unlabelled enzyme related protein and crude *N. gonorrhoeae* (gonococcus, i.e., G.C.) lysates. At the 25% displacement level, the assay can detect 40 nanograms of subunit and can also detect the enzyme in as little as 400 nanograms of bacterial lysate. Table I shows the specificity of the radioimmunoassay for the enzyme found in *N. gonorrhoeae* cultures. Lysates of *Proteus vulgaris, Escherichia coli,* and *Candida albicans* show no reactivity. A *Staphylococcus epidemidis* lysate is weakly reactive at protein concentrations 120 times that used for the *N. gonorrhoeae* test. Purified dehydrogenase enzyme from *Aerobacter aerogenes* does not react. However, lysates from *N. meningitidis* are as potent as lysates from *N. gonorrhoeae* in displacing the labeled protein. Thus, the assay is specific for organisms in the *Genus Neisseria* when bacterial lysates are prepared as generally described.

TABLE I

Displacement of Radiolabelled Subunit from Rabbit Antiserum

| Sample | Protein (Micrograms) | % Displacement |
|---|---|---|
| Subunit | 0.04 | 25% |
| *N. gonorrhoea* lysate | 0.75 | 25% |
| *N. meningitidis* lysate | 0.75 | 25% |
| *S. epidermis* lysate | 90.0 | 25% |
| *P. vulgaris* lysate | 40.0 | <5% |
| *E. coli* lysate | 80.0 | <5% |
| *C. albicans* | 90.0 | <5% |
| Glycerol dehydrogenase (Purified from *A. aerogenes*) | 50.0 | <5% |

In general, the operable pH values for lysis and incubation seem to average between about 7–10 with the optimum apparently between about 8–9. Whereas incubation has been observed at temperatures approaching 0° C., the reaction rate is considerably increased as the temperature of the antiserum-lysate mixture is raised. This reaction rate appears to reach an optimum at about 50° C., but decreases quite rapidly beyond that figure. Accordingly, about 60° C. has been deemed to constitute a practical maximum temperature for incubation. However, the rate of reaction at room temperature has been found to be sufficiently rapid to justify the convenience of utilizing that temperature (20°–25° C.) for incubation.

Finally, it will be appreciated that, if desired, the antiserum can be immobilized on any type of substrate material which is inert toward the reactants. For example, glass or ceramic substrates are particularly useful and the antibodies can be immobilized thereto via physical adsorption or covalent bonding.

I claim:

1. A method for detecting Neisseria bacteria in a fluid sample via a radioimmunoassay technique consisting of the steps:
   (1) bringing radiolabelled 1,2-propanediol dehydrogenase or its subunit into contact with a lysate of the sample to be tested;
   (2) bringing an antiserum specific to 1,2-propanediol dehydrogenase into contact with the above and incubating the mixture;
   (3) separating the unlabelled and radiolabelled 1,2-propanediol dehydrogenase-antibody complexes from the uncomplexed reactants in said mixture; and then
   (4) monitoring either or both portions of the mixture for the presence of radiolabelled 1,2-propanediol dehydrogenase or its subunit.

2. A method according to claim 1 wherein said fluid sample is a human body fluid or exudate.

3. A method according to claim 1 wherein lysis and incubation are carried out at a pH between about 7–10.

4. A method according to claim 1 wherein lysis and incubation are carried out at temperatures between about 0°–60° C.

5. A method according to claim 1 wherein said antiserum is immobilized on a substrate which is inert toward the reactants.

6. A method according to claim 5 wherein said antiserum is immobilized on said substrate via physical adsorption or covalent bonding.

7. A method according to claim 1 wherein said Neisseria bacteria are of the species *Neisseria gonorrhoeae*.

8. A method for detecting Neisseria bacteria in a fluid sample via a radioimmunoassay technique consisting of the steps:
   (1) preparing an antiserum specific to 1,2-propanediol dehydrogenase;
   (2) purifying 1,2-propanediol dehydrogenase or its subunit;
   (3) preparing radiolabelled 1,2-propanediol dehydrogenase or its subunit;
   (4) preparing a lysate of said fluid sample;
   (5) mixing and incubating said lysate with said antiserum and said radiolabelled and unlabelled 1,2-propanediol dehydrogenase or its subunit;
   (6) admixing an antiglobulin reagent which causes a precipitation of the 1,2-propanediol dehydrogenase-antibody complex or 1,2-propanediol dehydrogenase subunit-antibody complex, thereby separating them from the uncomplexed reagents; and then
   (7) monitoring the precipitate and/or the supernatant liquid for the presence of radiolabelled 1,2-propanediol dehydrogenase or its subunit.

9. A method according to claim 8 wherein said fluid sample is a human body fluid or exudate.

10. A method according to claim 8 wherein lysis and incubation are carried out at a pH between about 7–10.

11. A method according to claim 8 wherein lysis and incubation are carried out at temperatures between about 0°–60° C.

12. A method according to claim 8 wherein said antiserum is immobilized on a substrate which is inert toward the reactants.

13. A method according to claim 12 wherein said antiserum is immobilized on said substrate via physical adsorption or covalent bonding.

14. A method according to claim 8 wherein said Neisseria bacteria are of the species *Neisseria gonorrhoeae*.

* * * * *